(12) United States Patent
Glenn

(10) Patent No.: US 7,473,219 B1
(45) Date of Patent: Jan. 6, 2009

(54) FLEXIBLE FIBER OPTIC BRONCHOSCOPE ONE-WAY VALVE

(76) Inventor: Joshua P. Glenn, 9144 Rockrose Dr., Tampa, FL (US) 33647

( * ) Notice: Subject to any disclaimer, the term of this patent is extended or adjusted under 35 U.S.C. 154(b) by 1047 days.

(21) Appl. No.: 10/382,771

(22) Filed: Mar. 7, 2003

(51) Int. Cl.
*A61B 1/00* (2006.01)

(52) U.S. Cl. .................. 600/114; 600/120; 600/154; 600/159

(58) Field of Classification Search ............... 600/114
See application file for complete search history.

(56) References Cited

U.S. PATENT DOCUMENTS

| | | | |
|---|---|---|---|
| 4,586,491 A | 5/1986 | Carpenter | |
| 5,114,408 A * | 5/1992 | Fleischhaker et al. | 604/167.04 |
| 5,309,902 A | 5/1994 | Kee et al. | |
| 5,333,606 A | 8/1994 | Schneider et al. | |
| 5,333,607 A | 8/1994 | Kee et al. | |
| 5,598,840 A | 2/1997 | Iund et al. | |
| 5,628,306 A | 5/1997 | Kee | |
| 6,016,800 A | 1/2000 | Century | |
| 6,029,657 A | 2/2000 | Century | |
| 6,041,775 A | 3/2000 | Century | |
| 6,086,529 A | 7/2000 | Arndt | |

* cited by examiner

*Primary Examiner*—Linda C Dvorak
*Assistant Examiner*—Matthew J Kasztejna
(74) *Attorney, Agent, or Firm*—John D. Gugliotta, PE, Esq.

(57) ABSTRACT

A flexible fiber optic bronchoscope with one-way valve is provided in which a unidirectional flow control valve is inserted between the bronchoscopic manifold port and the sealing cap. A compressible diaphragmatic seal with radial slits separate resiliently returnable valve flaps that deformably compress around the shaft of any inserted conduit. A circumscribing housing for typically affixing along a lower receiving ring to the bronchoscopic manifold port to which the sealing cap would normally be attached. An upwardly extending, annular attachment protuberance thereby provides the attachment for the conventional sealing cap.

6 Claims, 2 Drawing Sheets

FLEXIBLE FIBER OPTIC BRONCHOSCOPE ONE-WAY VALVE

RELATED APPLICATIONS

The present invention was first described in Disclosure Document Registration filed under 35 U.S.C. §122 and 37 C.F.R. §1.14, but not yet returned. There are no previously filed, nor currently any co-pending applications, anywhere in the world.

BACKGROUND OF THE INVENTION

1. Field of the Invention

The present invention relates generally to a flexible fiberoptic bronchoscope and, more particularly, to a unidirectional flow control valve particularly adapted for use with a bronchoscope manifold.

2. Description of the Related Art

Bronchoscopy includes an evaluation of the respiratory system, including voice box (larynx), wind pipe (trachea), and the airways (bronchi) for evidence of any abnormality. The physician can see these structures during different stages of the breathing cycle. He/she can also take pictures and record the images on video. This is helpful when explaining the results of the procedure to the patient and/or family. The video image is also helpful for the physician to monitor the progress of any abnormality found.

Bronchoscopy is usually performed by a pulmonologist, respiratory therapist or a thoracic surgeon. Although a bronchoscope does not allow for direct viewing and inspection of the lung tissue itself, samples of the lung tissue can be biopsied through the bronchoscope for examination in the laboratory.

There are two types of bronchoscopes—a flexible fiber optic bronchoscope and a rigid bronchoscope. Since the 1960s, the fiber optic bronchoscope has progressively supplanted the rigid bronchoscope because of overall ease of use. In addition, patients typically do not require general anesthesia for fiberoptic bronchoscopy while a rigid bronchoscopy requires additional medical personnel to perform the procedure because general anesthesia is required. During the bronchoscopy, the examiner can see the tissues of the airways either directly by looking through the instrument or by viewing on a TV monitor.

Depending on the indication the examiner will choose between the flexible fiber optic bronchoscope or the rigid bronchoscope. For example, if a patient were coughing up large amounts of blood, a rigid bronchoscope is used since it has better optics for viewing and large suction channel.

Complications of bronchoscopy to the patient are relatively rare and most often minor. These can include: Nose bleeding (epistaxis); Vocal cord injury Irregular heart beats; Lack of oxygen to the body's tissues; Heart injury due to the medication or lack of oxygen; Bleeding from the site of biopsy; Punctured lung (pneumothorax); Damage to teeth (from rigid bronchoscopy); or complications from pre-medications or general anesthesia.

However, generally not considered in the use of fiberoptic bronchoscopes are the potential complications to the pulmonologist or a thoracic surgeon performing the procedure. Many aspects in the use of bronchoscopes can allow for escape and dispersal of the patient's body fluids past the insertion manifold used to guide the bronchoscope due to positive end expiratory pressure. By way of example of such hazards:

Washing—Squirts of salt water (saline) are injected through the bronchoscope into the area of interest and the fluid is then suctioning back. This process is repeated several times to obtain adequate samples, which are then submitted to the laboratory for analysis.

Needle aspiration—A small needle is inserted into the airway and through the wall of the airway to obtain samples outside of the airway for analysis under a microscope.

Forceps biopsy—Forceps may be used to biopsy either a visible lesion in the airway or a lung lesion. Abnormal tissue that is visible in the airway is usually easily biopsied. However, a mass that is in the lung tissue is deep within the lung and usually requires a biopsy using special x-ray guidance (fluoroscopy). Specimens obtained are sent to a pathologist for inspection under a microscope.

In a bronchoalveolar lavage (BAL), the physician injects a small amount of saline through the bronchoscope into the airways and then sucks it back through the suction port of the bronchoscope. The fluid obtained contains saline plus secretions from the lung, bacteria (if present), cells, etc. This sample is sent to the laboratory for various tests.

Further, bronchoscopy is performed in various settings, including same-day outpatient bronchoscopy suite, operating room, hospital ward, and/or intensive care unit. In any of these settings, and with any of these procedures, a real risk of contamination or infection of the pulmonologist or a thoracic surgeon performing the procedure is present due to splashing of fluid secretions, either during the procedure or at the end during the removal of the instrument.

A search of the prior art did not disclose any patents that read directly on the claims of the instant invention; however, the following references were considered related.

U.S. Pat. No. 6,086,529 describes a bronchoscope manifold with compressible diaphragmatic valve.

U.S. Pat. No. 6,041,775 describes a intrapulmonary aerosolizer.

U.S. Pat. No. 6,029,657 describes a intrapulmonary aerosolizer.

U.S. Pat. No. 6,016,800 describes a intrapulmonary aerosolizer

U.S. Pat. No. 5,628,306 describes a respiratory manifold with accessory access port.

U.S. Pat. No. 5,598,840 describes a sealed ventilation circuit interface system.

U.S. Pat. No. 5,333,607 describes a ventilator manifold with accessory access port.

U.S. Pat. No. 5,333,606 describes a endotracheal respiration system.

U.S. Pat. No. 5,309,902 describes a respiratory support system and suction catheter device.

And, U.S. Pat. No. 4,586,491 describes a bronchoscope with small gauge viewing attachment.

Consequently, a need has been felt for providing an apparatus and method of protecting the pulmonologist or a thoracic surgeon performing the procedure from contamination by a patient's bodily fluids.

SUMMARY OF THE INVENTION

It is therefore an object of the present invention to provide an bronchoscope manifold for use with a flexible fiber optic bronchoscope.

It is a feature of the present invention to provide an improved unidirectional flow control valve particularly adapted for use with a bronchoscope manifold.

Briefly described according to one embodiment of the present invention, a flexible fiber optic bronchoscope with one-way valve provided in which a unidirectional flow control valve is inserted between the bronchoscopic manifold port and the sealing cap. A compressible diaphragmatic seal with radial slits separate resiliently returnable valve flaps that deformably compress around the shaft of any inserted conduit. A circumscribing housing for typically affixing along a lower receiving ring to the bronchoscopic manifold port to which the sealing cap would normally be attached. An upwardly extending, annular attachment protuberance thereby provides the attachment for the conventional sealing cap.

An advantage of the present invention is that it protects the pulmonologist or a thoracic surgeon performing the procedure from contamination by a patient's bodily fluids during removal of the flexible fiber optic bronchoscope.

BRIEF DESCRIPTION OF THE DRAWINGS

The advantages and features of the present invention will become better understood with reference to the following more detailed description and claims taken in conjunction with the accompanying drawings, in which like elements are identified with like symbols, and in which:

DESCRIPTION OF THE PREFERRED EMBODIMENTS

Figure 1:
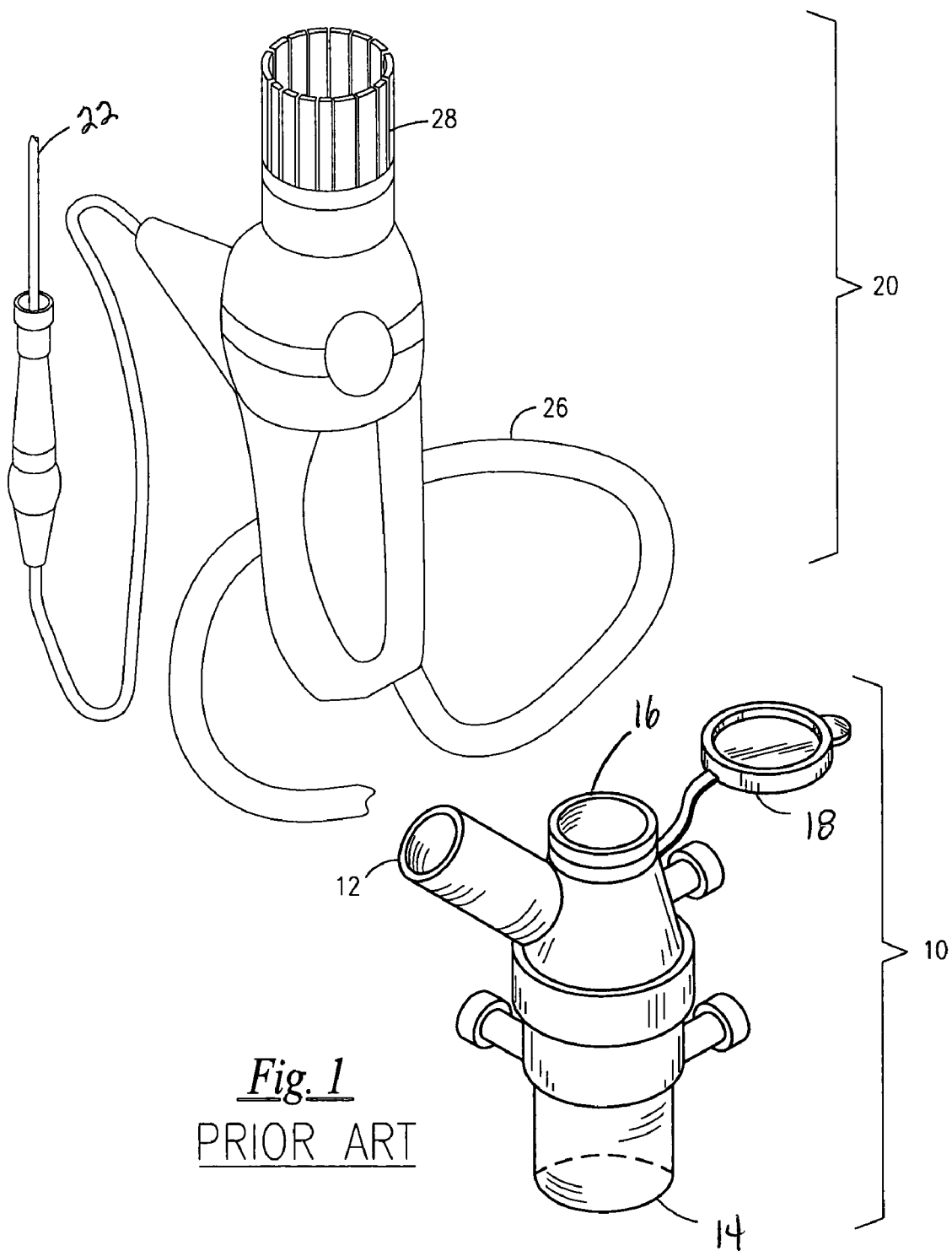
FIG. 1 is a perspective view of Fiberoptic Bronchoscope 20 used in conjunction with a bronchoscopic manifold 10 according to the PRIOR ART.

In order to describe the complete relationship of the invention, it is essential that some description be given to the manner and practice of functional utility and description of fiberoptic bronchoscopes in general as it appears in the prior art, shown in FIG. 1. Generally illustrated, a bronchoscopic manifold 10 having a tubular passage opening to the hollow body of the manifold consisting of a tubular conduit open to the manifold and exterior to the manifold. A mechanical ventilation port 12 opens to the manifold interior and allows connection to a mechanical ventilator (not shown) through commercially available mechanical ventilator connection tubing (not shown). An endotracheal tube connection port 14 opens to the manifold interior and is located in an orthogonal position to the mechanical ventilation port 12 as a patient connection, and generally connects to an endotracheal tube. The endotracheal tube attachment collar (not shown) is also customarily used and allows the manifold to rotate along freely the central axis or be fixed along the central axis. A bronchoscopic manifold port 16 is located opposite and in line along the central axis to the endotracheal tube connection port 14 and open to the interior of the manifold. The external opening of the bronchoscopic manifold port 16 is usually covered by a commercially available bronchoscopic end cap 18 with attached sealing lid which may be opened and closed to allow the introduction and removal of a fiberoptic bronchoscope 20 and form a gas tight seal when closed. Secondary instrument ports are also generally available, located at an angle in relation to the central axis of the manifold and the bronchoscopic manifold port 16 to allow easy introduction of a secondary tubular instrument into the manifold and open to the interior of the manifold.

The fiberoptic bronchoscope 20 in general includes a video/light source 22 in addition to a camera connecting port 24 for connection to and access with a video camera (not shown). Both the light source and camera fiberoptic are transferred down a soft rubber conduit 26 past the bronchoscopic manifold port 16 and through the endotracheal tube into the patient.

1. Detailed Description of the Figures

Figure 2:
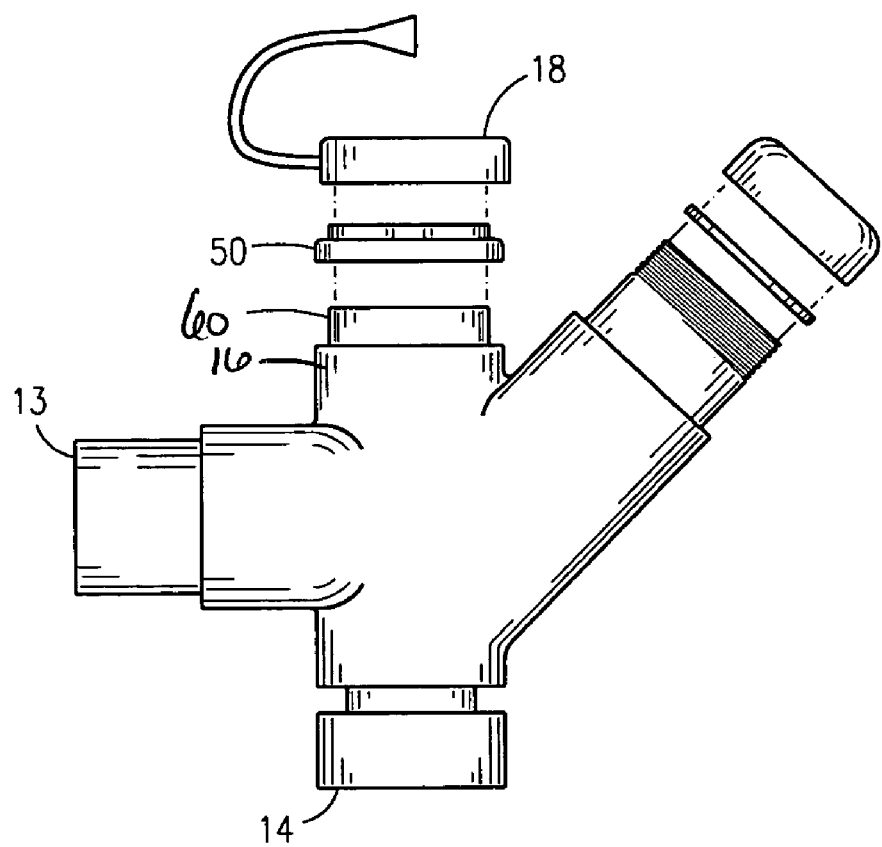
FIG. 2 is a side elevational view of a flexible fiber optic bronchoscope manifold with one-way valve incorporating the preferred embodiment of the present invention.

Referring now to FIG. 2, a flexible fiber optic bronchoscope with one-way valve is shown depicting the improvements of the present invention incorporated within a common type of connection to a bronchoscopic manifold 10. The external opening of the bronchoscopic manifold port 60 is covered by a unidirectional flow control valve 50, as is described in greater detail below. The unidirectional flow control valve 50 is inserted between the bronchoscopic manifold port 16 and the sealing cap 18. The cap 18 may be opened and closed to allow the introduction and removal of the fiberoptic bronchoscope. A fiberoptic bronchoscope is inserted through valve 50 and into the bronchoscopic manifold port 16 and advanced to be in the trachea. A secondary instrument is a commercially available tubular catheter device which may perform various tasks in the distal trachea. The secondary instrument may be an endobronchial blocker, a fiberoptic bundle, a small electronic instrument placed in the distal end of a catheter, a jet ventilation catheter or any device which may be placed with a small tubular conduit so as the internal diameter of the endotracheal tube and trachea is large enough to accept both the fiberoptic bronchoscope and secondary instrument. Upon removal of the bronchoscope, the flow control valve 50 is resiliently returning to cover the bronchoscopic manifold port 16 in a manner to eliminate discharge of fluid or secretions that may be forced outward as a result of any suction or mechanical agitation caused by the removal of the bronchoscope.

Figure 3:
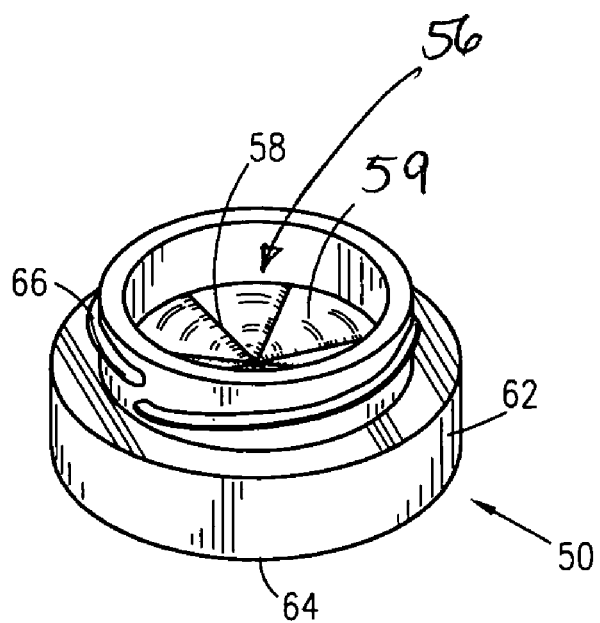
FIG. 3 is a perspective view of a manifold one-way valve for use therewith.

FIG. 3 illustrates the unidirectional flow control valve 50 that is inserted between the bronchoscopic manifold port 16 and the sealing cap 18. A compressible diaphragmatic seal 56 with radial slits 58 is shown. The slits 58 separate resiliently returnable valve flaps 59 that deformably compress around the shaft of any inserted conduit. A circumscribing housing 62 is shown for typically affixing along a lower receiving ring 64 to the bronchoscopic manifold port 16 to which the sealing cap 18 would normally be attached. An upwardly extending, annular attachment protuberance 66 thereby provides an attachment structure for the sealing cap 18.

2. Operation of the Preferred Embodiment

Typically a flexible bronchoscopy is NOT done under general anesthesia but the patient is given medications via an IV to obtain sedation (sleepy state). The patient is arousable from this deep sleep and is able to cough, sneeze or try to speak if directed. Numbing drops (Lidocaine) are instilled into the nose to numb the nose, back of the throat and this medicine is dropped though the bronchoscope to numb other structures such as larynx, trachea, bronchi, etc. as they are encountered during the procedure. Lidocaine prevents irritation, cough, sneeze, etc. Once the numbing medication takes effect the bronchoscope is inserted and the procedure takes place.

Once the intravenous (IV) line is in and all monitoring equipment is attached for continuous monitoring of the heart rate, blood pressure, and oxygen level in the blood. If needed, supplemental oxygen will be supplied either through a ½ inch tube inserted into the nostrils (cannula) or a facemask. Medication is then given through the IV to make the patient feel relaxed and sleepy for the flexible fiber optic bronchoscopy. If rigid bronchoscopy is to be performed, an anesthesiologist will be present to induce and monitor the general anesthesia. Once the bronchoscope is in the airway, an additional topical anesthetic will be sprayed into the airway for local anesthesia to minimize discomfort and coughing spells. The rigid bronchoscopy is inserted by mouth only.

Accordingly, the reader will see that the manifold for ventilation of medical and surgical patients of this invention can be used to allow simultaneous fiberoptic bronchoscopy and the introduction of a secondary tubular instrument into the trachea of intubated patient and affix the tubular secondary instrument in place forming a gastight seal using a torquable diaphragmatic seal. The manifold incorporates a minimum of four ports for connection of a mechanical ventilator to an endotracheal tube to allow fiberoptic bronchoscopy, and simultaneous airway instrumentation. Each port is designed to perform specific tasks and oriented in position to allow simultaneous ventilation, fiberoptic bronchoscopy and introduction and placement of a secondary tubular instrument under direct vision. In addition, the instrumentation port is designed with a perforated diaphragmatic seal in which the compressive force against the wall of the secondary instrument is adjustable by compressing the diaphragmatic seal between the threaded secondary instrumentation port and the threaded secondary instrumentation cap with an end hole so as to form a gas tight seal against a secondary tubular instrument placed through the instrument port and affix it in position. The secondary instrument port is oriented at an angle of 15 degrees to 70 degrees in relation to the bronchoscopy port to allow easy and timely introduction of the secondary tubular instrument into the body of the manifold. Furthermore, the manifold has the additional advantage in that it allows placement of a secondary tubular for long periods of time without movement by being locked into position by the sealing mechanism of the secondary instrument port.

The foregoing descriptions of specific embodiments of the present invention have been presented for purposes of illustration and description. They are not intended to be exhaustive or to limit the invention to the precise forms disclosed, and obviously many modifications and variations are possible in light of the above teaching. The embodiments were chosen and described in order to best explain the principles of the invention and its practical application, to thereby enable others skilled in the art to best utilize the invention and various embodiments with various modifications as are suited to the particular use contemplated. It is intended that the scope of the invention be defined by the Claims appended hereto and their equivalents. Therefore, the scope of the invention is to be limited only by the following claims.

What is claimed is:

1. A flexible fiber optic bronchoscope one-way valve for use with an otherwise conventional bronchoscopic manifold having a bronchoscopic manifold port covered by a sealing cap, wherein said cap may be opened and closed to allow the introduction and removal of the fiberoptic bronchoscope, said one-way valve comprising:
    a circumscribing housing for connection to said manifold port in place of said sealing cap along a lower receiving ring;
    an upwardly extending, annular attachment protuberance formed opposite said receiving ring for providing an attachment structure for the sealing cap of the bronchoscopic manifold port; and,
    a unidirectional flow control valve supported within said circumscribing housing;
    wherein when a fiberoptic bronchoscope is insertable through said flow control valve and into the bronchoscopic manifold port.

2. The flexible fiber optic bronchoscope one-way valve of claim 1, said unidirectional flow control valve comprises a compressible diaphragmatic seal with a plurality of radial slits.

3. The flexible fiber optic bronchoscope one-way valve of claim 2, wherein each said slit separates adjacent resiliently returnable valve flaps that deformably compress around any inserted conduit.

4. A removable one-way valve for use with an otherwise conventional bronchoscopic manifold having a bronchoscopic manifold port covered by a sealing cap, wherein said cap may be opened and closed to allow an introduction and a removal of a fiberoptic bronchoscope, said one-way valve comprising:
    a circumscribing housing for connection to said manifold point in place of said sealing cap along a lower receiving ring;
    an upwardly extending, annular attachment protuberance formed opposite said receiving ring for providing an attachment structure for the scaling cap of the bronchoscopic manifold port; and,
    a unidirectional flow control valve supported within said circumscribing housing;
    wherein said flow control valve is attached to the attachment for the removed sealing cap when a flexible fiber optic bronchoscope is insertable through said flow control valve and into the bronchoscopic manifold port for a medical procedure, said one-way valve is unattached from the attachment after the procedure so that the scaling cap can be therefore replaced back on the manifold port.

5. The flexible fiber optic bronchoscope one-way valve of claim 4, said unidirectional flow control valve comprises a compressible diaphragmatic seal with plurality of radial slits.

6. The flexible fiber optic bronchoscope one-way valve of claim 4, wherein each said slit separates adjacent resiliently returnable valve flaps that deformably compress around any inserted conduit.

* * * * *